US00PP25953P3

(12) United States Plant Patent
Swartz et al.

(10) Patent No.: US PP25,953 P3
(45) Date of Patent: Sep. 29, 2015

(54) RASPBERRY PLANT NAMED 'SAPPHIRE'

(50) Latin Name: ***Rubus ideaus* L.**
Varietal Denomination: Sapphire

(71) Applicant: FIVE ACES BREEDING LLC, Oakland, MD (US)

(72) Inventors: Harry Jan Swartz, Oakland, MD (US); Eva McCarthy, Faversham Kent (GB)

(73) Assignee: Five Aces Breeding LLC, Oakland, MD (US)

( * ) Notice: Subject to any disclaimer, the term of this patent is extended or adjusted under 35 U.S.C. 154(b) by 0 days.

(21) Appl. No.: 13/998,928

(22) Filed: Dec. 24, 2013

(65) Prior Publication Data

US 2015/0181783 P1 Jun. 25, 2015

(30) Foreign Application Priority Data

Mar. 18, 2013 (QZ) ..... PBR 2013/0882

(51) Int. Cl.
*A01H 5/00* (2006.01)

(52) U.S. Cl.
USPC ..... Plt./204

(58) Field of Classification Search
USPC ..... Plt./204
See application file for complete search history.

*Primary Examiner* — Annette Para
(74) *Attorney, Agent, or Firm* — Rosenberg, Klein & Lee

(57) ABSTRACT

The present invention is a new and distinct floricane fruiting red raspberry cultivar named 'Sapphire', which is capable of producing large, attractive, flavorful and firm fruit which has exceptional consumer appeal characteristics. The cultivar is characterized by its thorniness throughout the plant, as described herein, lack of fall or primocane fruiting, its strong and distinctive flavor and firmness and its very large fruit size, weight and morphology, specifically its truncated conic, very uniform, fruit shape with minimal bulginess in its basal region or on its receptacle. 'Sapphire' plants are very productive in regions having sufficient chilling to produce sufficient spring bud break. Its high yield, firmness, storage ability and large size make 'Sapphire' economical to pick mid to mid late season floricane variety for shipping.

10 Drawing Sheets

PRIORITY CLAIM

This invention claims priority under 35 U.S.C. §119(f) of application number 2013/0882 filed on 18 Mar. 2013 at the European Community Plant Variety Office (CPVO).

FIELD OF THE INVENTION

This invention concerns a new and distinct cultivar of floricane fruiting raspberry plant with a botanical name of *Rubus ideaus* L. The new cultivar is distinguished from other cultivars by its combination of fruit firmness, size, flavor and attractiveness and plant productivity. 'Sapphire' is thereby suitable for premium fresh fruit marketing in commercial production areas which rely on floricane cultivars with normal chilling requirements.

DESCRIPTION OF RELATED PRIOR ART

Several cultivars of floricane fruiting (commonly known as "spring bearing") raspberry plants are known which have either large sized, firm or attractive fruit. For instance, raspberry cultivars named 'Glen Ample', 'Josephine', 'Driscoll Maravilla', 'Cascade Bounty', 'Adele', 'Marcianna', 'Wakefield', 'DrisRaspFour', 'Crimson Giant', and 'DrisRaspThree', have been described in U.S. Plant Pat. Nos. 11,418, 12,173, 14,804, 18,246, 20,773, 21,007, 21,185, 22,731, 23,375 and 23,477, respectively and 'Georgia' U.S. Pat. No. 20070261142. The new and distinct cultivar of the present invention is a raspberry plant named 'Sapphire'. This cultivar differs from 'Josephine', 'Driscoll 'Driscoll Maravilla', 'Marcianna', 'DrisRaspFour', 'Crimson Giant' and 'DrisRaspThree' in bearing fruit only in the spring while the other cultivars can also produce fruit on their primocanes in the fall. 'Sapphire' canes are thorny, distinguishing it from 'Glen Ample' and 'Georgia' which are thornless, and 'Adele', which is minimally thorny and has spines which are smaller and lighter colored then 'Sapphire'. 'Driscoll Maravilla' has spines similar in number and size to 'Sapphire', however, the spines on 'Sapphire' are darker in color, and the color is more uniform. 'Sapphire' fruit is bright red in color when ripe, while other floricane-crop only cultivars 'Wakefield' and 'Crimson Giant' are dark red when ripe, resembling over ripe 'Sapphire' fruit. 'Cascade Bounty' is a floricane variety with similar thorn coloration and size. 'Sapphire' thorns are more numerous (approximately double at the base of the plant) and 'Sapphire' fruit is larger, firmer and more conic than the medium sized and round 'Cascade Bounty'

ORIGIN OF THE NEW CULTIVAR

The new cultivar of spring bearing red raspberry originated from a controlled cross by Five Aces Breeding LLC of Oakland, Md. at rented glasshouse facilities in College Park, Md. The cross, designated: "DB" was Octavia (unpatented)× XFU-12vf (unpatented) and was made in the winter of 2002. 'Octavia' is a premium late season, floricane fruiting, red raspberry cultivar with several desirable fruit quality attributes, including fruit size and reasonable fruit firmness. 'XFU-12vf' also has several desirable fruit attributes, such as flavor and large fruit size, but is relatively soft. XFU-12vf is a cross of TU-2 (unpatented)×'Caroline' (U.S. Plant Pat. No. 10,412). TU-2 is a thorny sibling of the thornless spring bearing cultivar 'Georgia' (U.S. Pat. No. 20070261142). This year of crossing was designated "B" as part of the Five Aces Breeding Certified Raspberry Breeding Program. The seed from this cross was exported to the United Kingdom, germinated and grown by Edward Vinson Ltd at their Kemsdale Farm, Faversham, Kent United Kingdom. The present invention was second seedling of the BDB progeny selected from the floricane seedling field in July 2005 and was thereafter designated "-12vf". Thus, the complete breeding designation of 'Sapphire' is "BDB-12vf". There are no known or used synonyms for "BDB-12vf".

SUMMARY OF THE NEW CULTIVAR

This application relates to a new and distinct red fruited, floricane fruiting, raspberry cultivar, botanically known as *Rubus ideaus* L. The following characteristics are outstanding:

1. Production of floricane fruit which has a rare combination of commercial firmness, flavor, light color and attractiveness.
2. In all the areas of test of this selection, the fruit is larger than all commercial floricane bearing cultivars known to applicants.
3. With the exception of 'Glen Ample' with equal productivity, 'Sapphire' plants are more productive than other floricane fruiting cultivars tested in the United Kingdom; 'Glen Ample' fruit is commercially grown, but is much smaller in fruit size.

These characteristics make 'Sapphire' suitable as a midsummer floricane fruiting type for premium fresh fruit marketing in commercial production areas worldwide. As 'Sapphire' floricanes require more than 1000 hours of winter chilling for good bud break, 'Sapphire' should not be trusted to produce a crop in Mexico, the southern U.S. or south of Watsonville, Calif. Floricane fruit production has not been tested in areas that experience severe subfreezing temperatures, therefore, no claims are made concerning cold hardiness below −12° C. (10° F.)

The following characteristics are useful in distinguishing this cultivar from other cultivars and can be useful for cultivar identification. Plants used for these observations were grown in uncrowded conditions and in full sunlight.

1. 'Sapphire' plants do not produce a fall or primocane crop, even when given 160 days of good growing conditions. Floricanes require over 1000 hours of exposure to temperatures between 32° and 50° F. to have adequate bud break for a full spring crop.
2. The initial or primary fruit is conic; on average, the primary fruit is 25% longer than wide. Round type fruit, for example: 'Josephine' and 'Driscoll Maravilla', have primary fruit with a ratio of width to length within 10% of 1 to 1. Fruit size of primary fruits grown in the United Kingdom was 3.19 cm. in length and 2.55 cm. in width, with an average fruit weight of 8.3 grams. Thus, 'Sapphire' fruit size and weight is unusual for most raspberry genotypes, and rare in those with the combination of fruit quality traits which allow commercial production and shipping.
3. Thorns are numerous and found in greater abundance on the base of the plant as is normal for some varieties in the species. However, unlike a large majority of varieties, thorns are also abundant throughout the plant including petioles and peduncles. The coloration of the thorns on primocanes is typical of 'Sapphire' in different locations and, although this coloration is found in other cultivars, thorn color can be used to distinguish 'Sapphire' from some other cultivars. Thorn coloration is consistently deep grayed purple (1995 Royal Horticultural Society Color Plate No. 183A) and the coloration extends about 1 mm. in an oval into the surrounding cane. Thorn color deepens to The 1995 Royal Horticultural Society Color Plate No. 187A in the fall and in well lighted areas of the canes. Thorns are generally 2 mm. in length, relatively thin and slightly downward pointed. Less than 10% of the thorns on canes are minute or significantly reduced in size.

BRIEF DESCRIPTION OF THE PHOTOGRAPHS

The accompanying photographs show typical characteristics of the new variety:

FIG. 1. shows a basal section of a 'Sapphire' primocane with The 1995 Royal Horticultural Society Color Plate No. 144 for cane color and 183 for thorn color.

FIG. 2. shows an apical section of a 'Sapphire' primocane with a red blush and The 1995 Royal Horticultural Society Color Plate No. 184B and slightly darker colored apical spines with Royal Horticultural Society Color Plate No. 187A and a cm. measuring stick.

FIG. 3. shows the two surfaces of 'Sapphire' primocane leaves and The 1995 Royal Horticultural Society Color Plate Nos. 193C and 143A and a cm. measuring stick.

FIG. 4. shows a 'Sapphire' flowering truss at flowering and with the leaves removed and a 1 ft. long measuring stick.

FIG. 5. shows a 'Sapphire' fruiting truss in a tunnel in early season.

Figure 6:
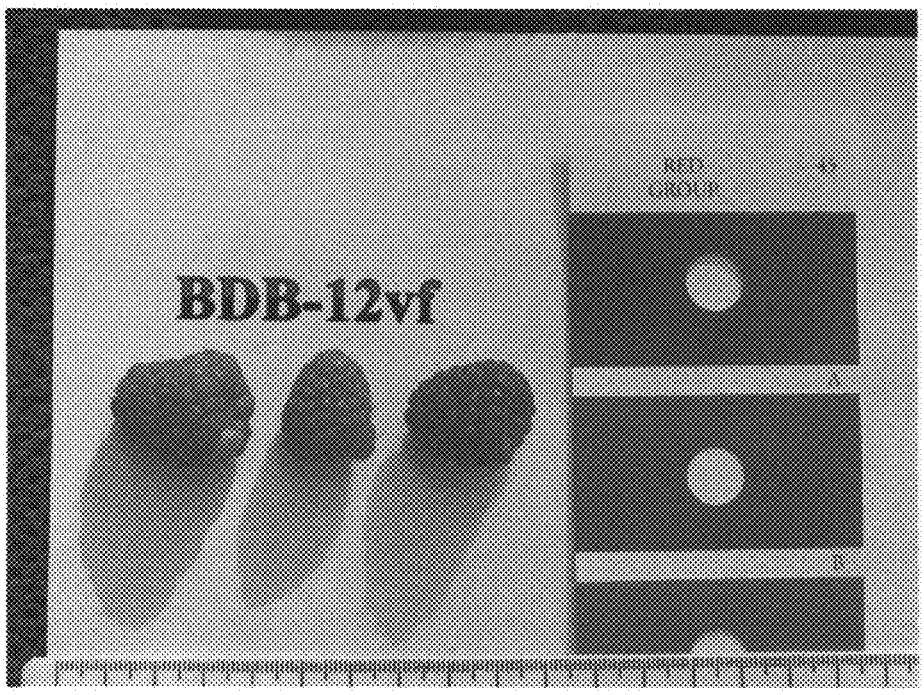

FIG. 6. shows three mid to late season fruit of 'Sapphire' and a cm measuring stick with mm gradations and The 1995 Royal Horticultural Society Color Plate No. 45A-B.

Figure 7:
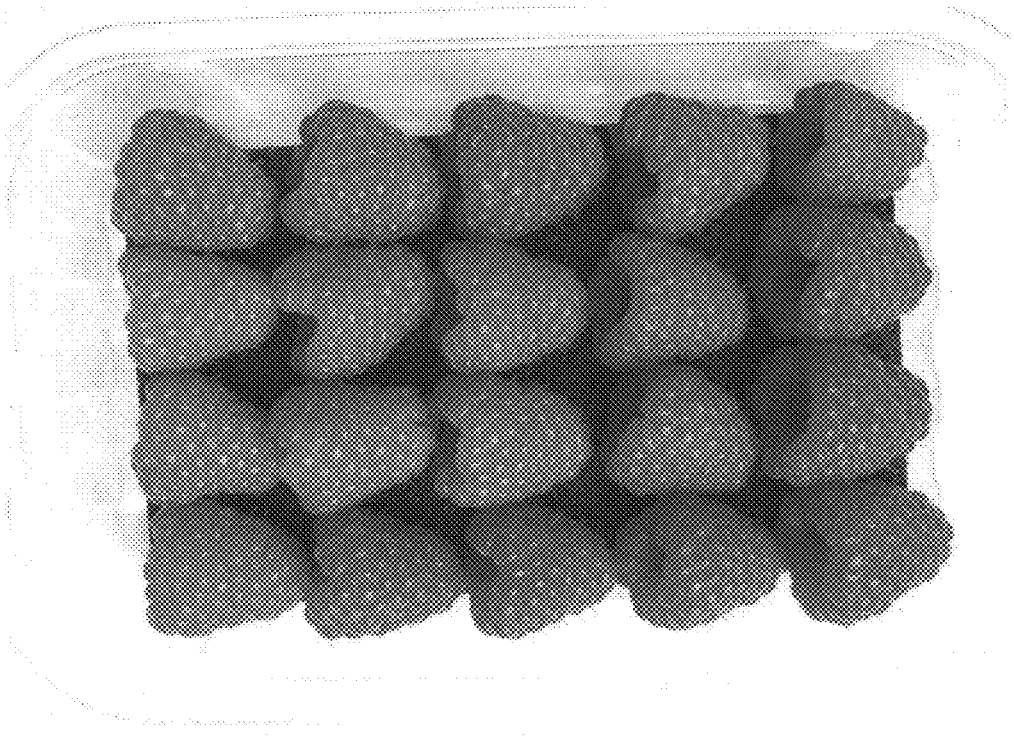

FIG. 7. shows early-midseason 'Sapphire' fruit in a pint clamshell.

Figure 8:
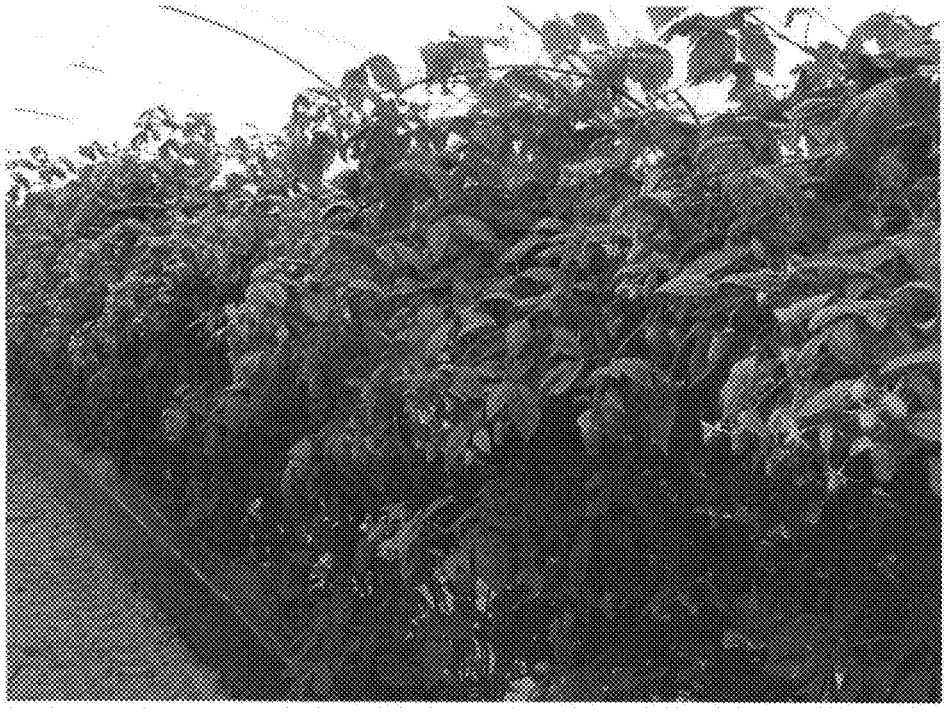

FIG. 8. shows a row of fruiting 'Sapphire' floricanes as in-ground plants grown in a tunnel.

DESCRIPTION OF THE NEW CULTIVAR

The following is a detailed description of 'Sapphire', the new cultivar, including fruit production, together with the cultivar's morphological characteristics. 'Sapphire' is a *Rubus idaeus* hybrid and would be botanically classified in that species commonly referred to as red raspberries. The characteristics of the cultivar were compared with other standards used in the United Kingdom and Mid-Atlantic Region of the U.S. The description is based on information provided by cooperating growers from plants grown in fields at Faversham, Kent, and Reading, Berkshire, England, and from plants grown in the Five Aces Breeding greenhouses at Oakland, Maryland, United States. As these climates differ, particularly in temperatures experienced in the growing season, we believe the description of 'Sapphire' will be consistent in other locations.

'Sapphire' produces a moderate number of root- and crown- suckers (19 per 10 gallon pot on one-year old tissue culture plants), more than 'Anne' and 'Josephine', but less than 'Georgia' and 'Glen Ample'. During the growing season, canes are light green colored (1995 Royal Horticultural Society Color Plate No. 144B) (FIG. 1) with a red blush (1995

Figure 2:
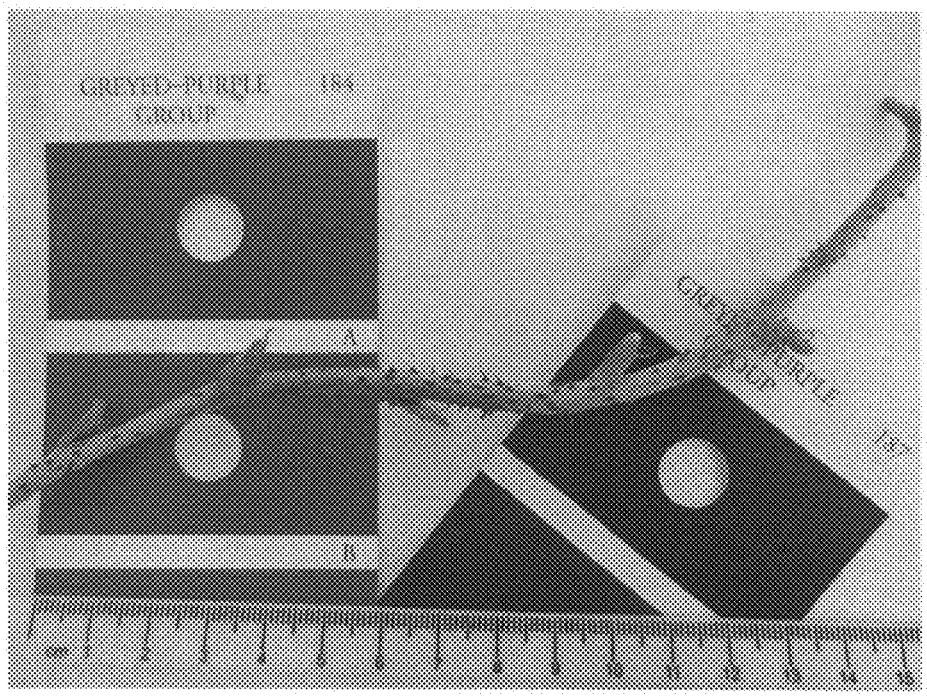

Royal Horticultural Society plate No. 184B) on less than 30% of the cane during the early summer (FIG. 2). Canes are usually unbranched and erect by the second year of a plant's growth. Total node of internodes per cane averaged 54 for first year tissue culture plants. By comparison, 'Josephine' produces 45 to 48 nodes per cane, on older adult or tissue culture produced first year plants. Growth of first year plants is moderately vigorous, reaching on average 82.5 inches in uncrowded conditions in tunnels. Internode length at 30 cm. above ground in well lighted plants without floricanes is 6.2 cm. Cane diameter at the same position was 0.85 cm. Canes have a moderate and noticeable waxiness, a finger rub leaves a visible mark due to removal of the wax or "bloom". In December or later, 'Sapphire' floricanes are blotchy light and moderately dark brown in color, resembling in hue The 1995 Royal Horticultural Society Color Plate Nos. 177D, 177C and 177B for the light, medium and darker brown patches respectively. Floricanes exfoliate to a slight amount, less than 10% in early winter.

Figure 1:
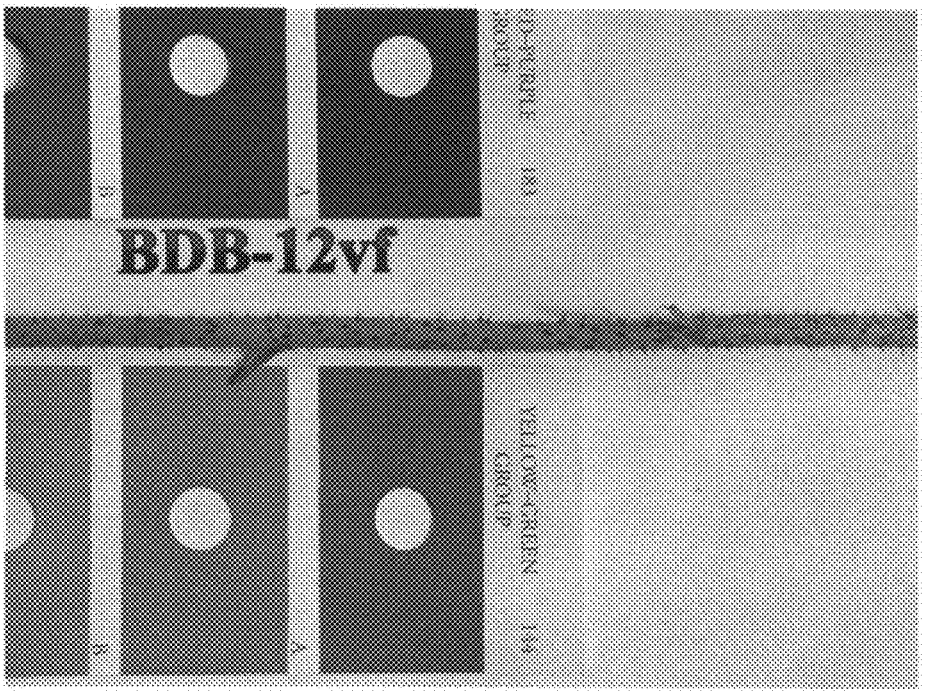

Thorns are abundant in density: ranging from 176 to 212 per internode with an average of 196.0 at 30 cm cane height and an average of 32.6 and range of 25 to 38 at the apex of the cane. Petioles averaged 12.6 thorns with a range of 7 to 21 per petiole. Thorn shape is straight, slightly downward pointing, and needle-like, (the length of the thorn is greater than twenty times its diameter) and length is approximately 2 mm (FIGS. 1 and 2). 'Sapphire' thorn color is grayed purple (1995 Royal Horticultural Society Color Plate No. 183A) in color throughout the spine (FIG. 1); including 1 mm of the surrounding epidermis of the cane. This thorn coloration of the cane is in an oval oriented with the long axis parallel to the axis of the cane. The color of the thorns turns darker red (FIG. 2) in the fall or earlier in full sunlight in the apical part of the cane (1995 Royal Horticultural Society Color Plate 187A) then brown in the dormant season (1995 Royal Horticultural Society Color Plate 177D), matching that of the overwintering floricanes. A similar pattern occurs with lateral buds, which are typical in size and shape of the species, bud color in the winter is dark brown (1995 Royal Horticultural Society Color Plate No. 177A).

Figure 3:
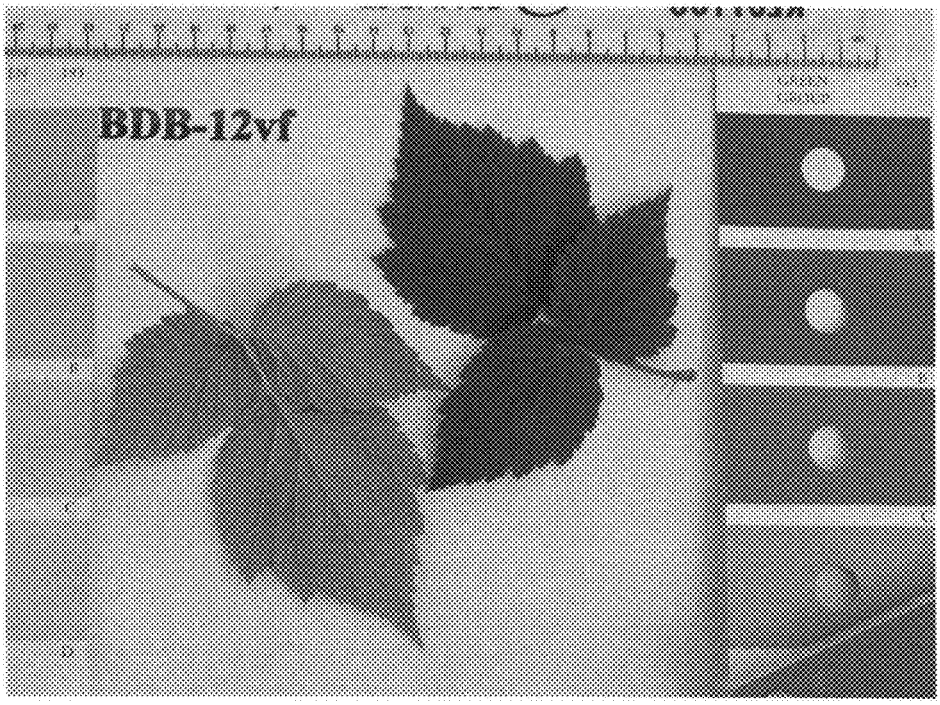

Typical of the species, 'Sapphire' leaf color and compoundedness are somewhat variable, being responsive to growing conditions, position on the plant, fertilization and vigor of the plant. In young plants, the lower surface of 'Sapphire' leaves is pubescent grey-green resembling The 1995 Royal Horticultural Society Color Plate No. 193C (FIG. 3). The upper surfaces of both pentafoliolate and trifoliolate leaves are dark green, most closely in hue to The 1995 Royal Horticultural Society Color Plate No. 143A in the greenhouse and 137A outdoors. Petiole and petiolule colors are the same as that of the primocane during the growing season, The 1995 Royal Horticultural Society Color Plate No. 144B, with occasional blush of similar to The 1995 Royal Horticultural Society Color Plate No. 184D. Senescing leaves have a green yellow color resembling The 1995 Royal Horticultural Society Color Plate No. 146A. Leaves abscise readily in October and November and simultaneous color changes and exfoliation of the cane are indicative of the change to a floricane and a strong response to short days and cool temperatures.

Vigorous plants have leaves that can be pentafoliolate through the growing season in protected culture, but mostly trifoliolate leaves occur, especially when grown outdoors in Oakland, Md., vigor is moderate or when short days occur and the internodes of the cane at the apex shorten in response to shorter light duration and cooler temperatures. Floricane trusses have almost exclusively trifoliolate leaves, with less than 10% monofoliolate leaves at the truss apex interspersed with apical fruit.

The pentafoliolate terminal leaflet is, on average, 7.0 cm. wide and 10.9 cm. long. The trifoliolate terminal leaflet is, on average, 8.5 cm. wide and 10.3 cm. long on primocanes and 5.2 cm. wide and 6.7 cm. long on floricane trusses. Monofoliolate leaves on floricane trusses are 3.2 cm. long and 1.2 cm. wide. The pentafoliolate maximum leaf width, measured from apex of a lateral leaflet to the opposite lateral leaflet apex is, on average, 18.5 cm. The trifoliolate maximum leaf width, measured from apex of the lateral leaflet to the opposite lateral leaflet apex is, on average, 16.1 cm on primocanes and 10.3 cm. on floricane trusses. The width of the largest basal lateral leaflet is 6.4 and 5.9 cm. for primocane pentafoliolate and trifoliolate leaflets, respectively; and 3.8 cm. on floricane trusses. The pentafoliolate leaf petiole, basal petiolule and apical petiolule lengths average 7.0 cm., 4.2 cm. and 2.2 cm., respectively, for a total length of 13.4 cm. The trifoliolate leaf petiole and terminal petiolule lengths averaged 4.0 cm. and 2.9 cm., respectively, on primocanes and 4.0 and 1.6 cm. on floricane trusses. For floral trusses, monofoliolate leaf petioles average 0.5 cm. in length. Lateral leaflets are sessile and join at the petiole apex with the apical leaf petiolule (FIG. 3). Leaf serration is moderately complex sawtooth but 'Sapphire' moderate laminar puckering and veination pattern are common for most cultivars of red raspberry and cannot be used to distinguish this cultivar.

Figure 4:
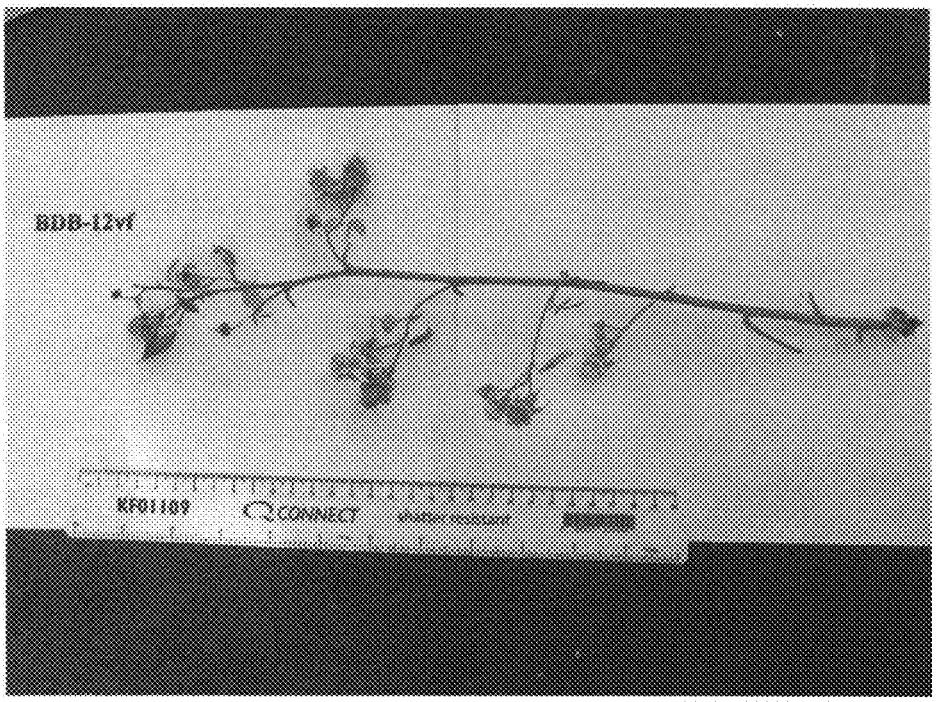

Flowers do not appear on primocanes of adult 'Sapphire' plants. After chilling typical of spring bearing cultivars of the species, over 1000 hours of temperatures between 32° F. and 50° F., lateral buds break and floral trusses are formed which average 11.8 nodes and 13.5 in. in length (FIG. 4). Of these 11.8 nodes, 4.9 have fruit on single or branched peduncles averaging 1.5 cm. in length. Peduncles have, on average, 26.3 minute, but fully colored, thorns. Fruit number per truss is 14.4 flowers. Thus, flower trusses are typical cymose clusters on a raceme with the apical flower on the main truss axis and the apical or "king" flower on the lateral compressed axes flowering first. The flowering sequence, by node, progresses from the apex first, with several fruit ripening at that position, then starting at the most basal nodes then acropetally toward the apex (FIG. 5).

The unscented flower morphology and early fruit morphology is typical of most red raspberry cultivars, having five white (1995 Royal Horticultural Society Color Plate No. 155D) petals that average 0.68 cm. long, 0.33 cm. wide; petals abscise after pollination. Flowers have five 0.85 cm. long, 0.5 cm. wide at the base triangular grey green sepals (1995 Royal Horticultural Society Color Plate No. 194B). Sepals are longer on primary fruits. Flowers have on average 58.8 pistils on smaller midseason fruit and a similar number of anthers, 59.2; none of these traits can be used to identify 'Sapphire'.

Figure 5:
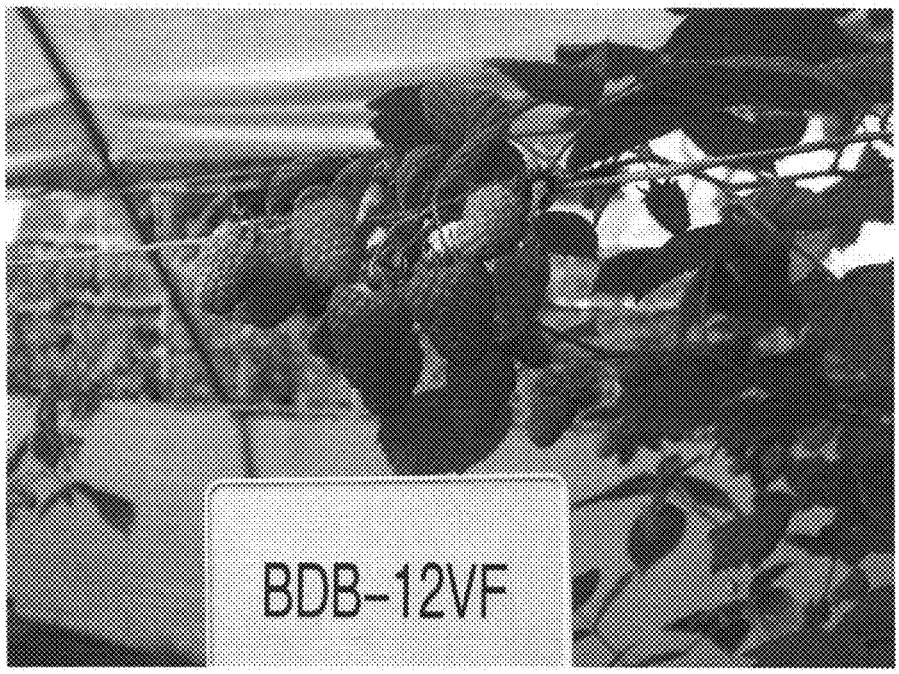
FIG. 5A shows a 'Sapphire' fruit on its side and a cm measuring stick with mm gradations indicating fruit length.
FIG. 5B shows a 'Sapphire' fruit resting on its top and a cm measuring stick with mm gradations indicating fruit width.
Figure 5A:
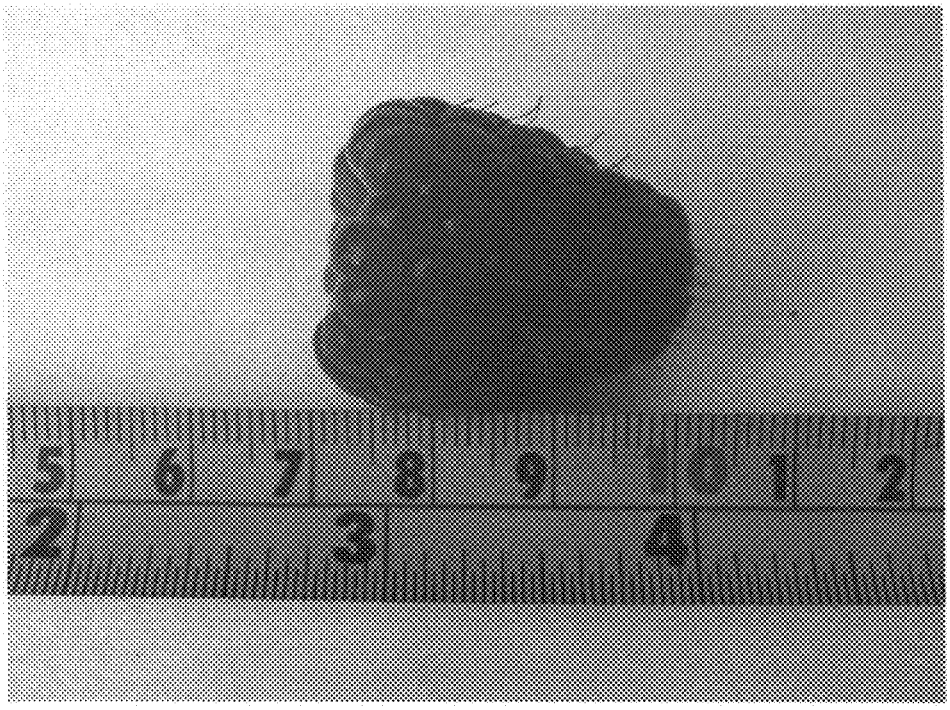
Figure 5B:
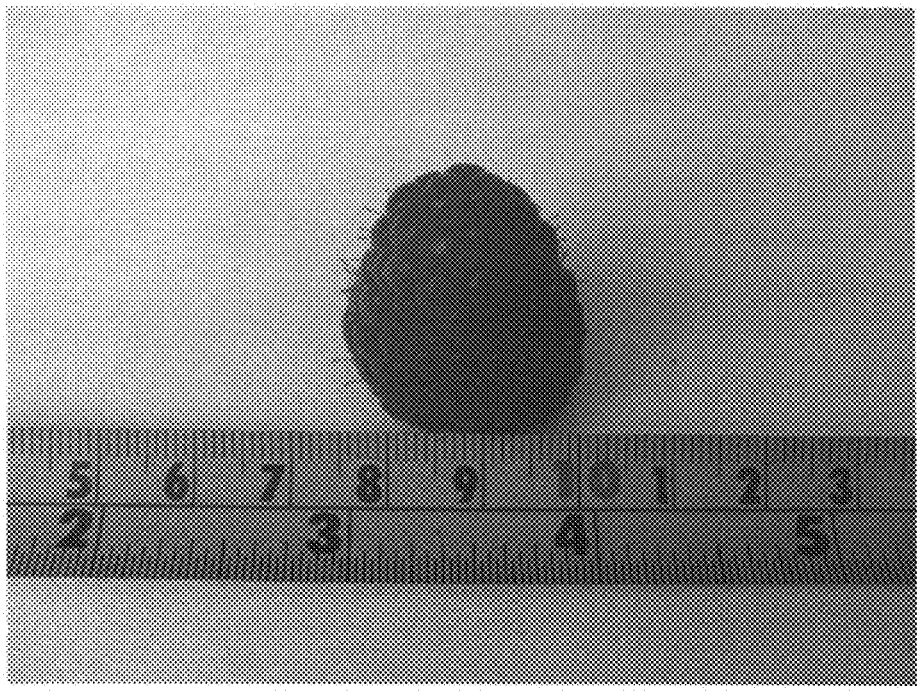

The initial or primary fruit are easily distinguishable by somewhat truncated conic shape for this variety at 12 days post pollination (FIGS. 4 and 5). Ripe larger fruit is smooth conic with a medium to large sized receptacle cavity averaging 1.3 cm. diameter. The initial mature fruit length was 3.19 cm (FIG. 5A) and width was 2.55 cm (FIG. 5B), producing an initial fruit width to length ratio of 4 to 5 (FIGS. 6 and 7), this ratio is smaller than 'Marcianna' and 'Jaclyn' two long fruited cultivars with a ratio above 5 width to 7 length. 'Sapphire', has a longer fruit than 'Josephine', 'Polka' and 'Driscoll Maravilla', which have more nearly round fruit and a ratio of 1 to 1. There are no irregularities to 'Sapphire' fruit shape or its underlying receptacle, a smooth cone which tapers to a point. With adequate width of the cavity, 50% of the fruit width, fruit removal does not result in distention of the drupelets of 'Sapphire', reducing splitting during commercial picking. Early fruit have 119 drupelets, and average 8.275 grams fresh weight. Later fruit are smaller and averaged 55 drupelets for forced plants in a trial in Oakland, Md. In a separate trial in England, average 'Sapphire' fruit weight across the season was 6.08 to 7.65 grams, depending on cane density (4 to 6 canes per meter). 'Sapphire' fruit are cohesive, but, unlike two other large-fruited fall bearing cultivars: 'Josephine' and 'Anne', it will not tear across the drupelets before individual drupelets separate from each other. Unlike 'Josephine' and 'Anne', 'Sapphire' fruit is not overly dusky or pubescent.

Fruit ripens beginning the second week in July in Kent, one month after flowering. In 2013, the 5%, 50% and 95% ripe dates for 'Sapphire' were: July 15, July 28 and August 9, respectively. For 'Glen Ample', a floricane producing standard for the area, the 5%, 50% and 95% ripeness dates were: July 10, July 26 and August 7, respectively. 'Glen Ample' is considered an early variety in the United Kingdom.

'Sapphire' fruit are medium red when ripe, closely resembling the hue of The 1995 Royal Horticultural Society Color Plate No. 45A (FIG. 6) and slightly lighter color when underripe, resembling The 1995 Royal Horticultural Society Color Plate No. 44B. When over ripe, fruit develops a darker red color. The fruit does not break down after at least 14 days in commercial cold storage. Flavor is sweet and the aroma is strong and characteristic of red raspberry. Spring ripened fruit was always rated above 'Marcianna', 'Driscoll Maravilla', and 'Tulameen' and significantly better than 'Glen Ample' (U.S. Plant Pat. No. 11,418) by a professional taste panel in the United Kingdom. The texture of the fruit is firmer than other eastern US-grown red raspberry cultivars known to us, with the exceptions of 'Josephine', 'Georgia' and 'Driscoll Maravilla', all with similar firmness. In the United Kingdom, 'Sapphire' fruit can be harvested every 72 hours between picking as contrasted to a required 36 hours between picking for 'Tulameen', the standard variety for mid-late season commercial fruit. In healthy plantings of 'Sapphire', class 2 or waste was 3.7 to 4.7% of total sound and sufficiently large fruit.

FRUIT PRODUCTION

'Sapphire' has been tested in commercial and garden plot trials in Kent and Berkshire in the United Kingdom (FIG. 8). The following data were collected in the summers of 2011 and 2013. In the Kent test, total yields in grams per plant were: 'Sapphire' 1652 (2011) and 1514 (2013). Total yield in grams per 'Glen Ample' plant was 1490 in 2011. In a separate trial in Berkshire, 'Sapphire' yield was 4.0, 5.3 and 6.9 kg/meters of row when 4, 5 or 6 floricanes were left in a meter of row, respectively. 6.9 kg/m of row would translate into 27,512 kg/ha=24,211 lbs./acre or 3,635 6⅔-lb trays per acre at 2.5 m. (8 ft.) spacing between rows. The plant is slightly susceptible to late season leaf rust (yellow rust). The plant's reaction to *Phyophthora fragariae* var *Rubi* root rot is unknown. When plants were excessively watered in winter in the United States glasshouse, no symptoms of root rot were observed in potted plants. In other genotypes, *Phytophthora* sp. was detected using a serological test and plants died. In the United Kingdom in plastic bags in soilless mix, some root rot symptoms occurred. *Phyophthora fragariae* var *Rubi* was not detected; however, an unidentified *Phytophthora* species was isolated from infested plants.

'Sapphire' can be asexually propagated by tissue culture or by root suckers. No off-type plants have been observed in the history of asexual propagation of this cultivar by either method.

What is claimed:

1. A new and distinct spring bearing red raspberry plant known as 'Sapphire' as described herein, illustrated and identified by the characteristics set forth above.

* * * * *